United States Patent [19]
Crow

[11] Patent Number: 6,106,966
[45] Date of Patent: Aug. 22, 2000

[54] SINGLE-CRYSTAL OXYGEN ION CONDUCTOR

[75] Inventor: Steven Collins Crow, Conifer, Colo.

[73] Assignee: The Arizona Board of Regents on behalf of the University of Arizona, Tucson, Ariz.

[21] Appl. No.: 09/115,476

[22] Filed: Jul. 15, 1998

Related U.S. Application Data

[63] Continuation of application No. PCT/US97/00977, Jan. 17, 1997.
[60] Provisional application No. 60/010,192, Jan. 18, 1996.
[51] Int. Cl.$^7$ .................................................... H01M 8/12
[52] U.S. Cl. ............................ 429/32; 429/33; 429/40; 204/421; 205/634
[58] Field of Search .............................. 429/33, 40, 44, 429/46, 26, 32; 204/426, 427, 421; 205/634

[56] References Cited

U.S. PATENT DOCUMENTS

| | | | |
|---|---|---|---|
| 3,316,163 | 4/1967 | Oser | 204/129 |
| 4,462,891 | 7/1984 | Lawless | 204/427 |
| 4,851,303 | 7/1989 | Madou et al. | 429/13 |
| 5,328,779 | 7/1994 | Tannenberger et al. | 429/32 |
| 5,518,830 | 5/1996 | Worrell et al. | 429/31 |
| 5,871,859 | 2/1999 | Parise | 429/26 X |

OTHER PUBLICATIONS

Kaneko et al. Conductivities of Yttria–Doped Zirconia Electrolytes, Proc. of the Third International Symposium on SOFC (1993), pp. 31–37, (month unknown).

*Primary Examiner*—Stephen Kalafut
*Attorney, Agent, or Firm*—Antonio R. Durando

[57] ABSTRACT

A single-crystal solid oxide material, rather than a polycrystalline ceramic, is used for electrolytic and fuel-cell applications. For the electrolytic production of oxygen from carbon dioxide, a yttria-stabilized zirconia crystal is coated with platinum electrodes and encased in a platinum structure to provide a thermally stable electrolytic cell. A multilayered device is constructed by stacking crystals and spacers in alternating arrangement and by plumbing the active surfaces of the crystals in parallel through perforations drilled directly in the solid-oxide crystals, so that manifolding and sealing problems are minimized.

14 Claims, 17 Drawing Sheets

SINGLE-CRYSTAL OXYGEN ION CONDUCTOR

RELATED APPLICATIONS AND GOVERNMENT RIGHTS

This application is a continuation of PCT/US97/00977, filed Jan. 17, 1997, which is based on U.S. Provisional Application No. 60/010,192, entitled "Crystal Oxygen Ion Conductor," filed by the same inventor on Jan. 18, 1996, both commonly owned with the present application.

The U.S. Government has a paid-up license in this invention and the right in limited circumstances to require the patent owner to license others on reasonable terms as provided for by the terms of Grant No. NGT 10035 awarded by NASA.

BACKGROUND OF THE INVENTION

1. Field of the Invention

This invention pertains in general to solid oxides for fuel cells and electrolyzers. Specifically, the invention relates to the use of single-crystal zirconia for the electrolytic production of oxygen and carbon monoxide from carbon dioxide, particularly in the atmosphere of Mars.

2. Description of the Prior Art

About 95 percent of the mass of the atmosphere of Mars is carbon dioxide. Accordingly, it has been a goal of space technology to develop a conversion process for separating oxygen from the carbon dioxide and to provide the oxygen in forms useful for propulsion and/or life support.

A prior-art process for accomplishing that goal has been to combine hydrogen with the carbon dioxide to produce methane and water, and then electrolyze the water to recover some hydrogen and produce the oxygen. The first stage of the process requires a catalytic reactor, while the second stage is carried out through traditional water electrolysis. The process requires a continuous feed of hydrogen supplied from earth and stored for use, which is very hard to achieve under all conditions. The inherent difficulty with hydrogen storage lies at the level of atomic physics, rather than engineering, in the fact that hydrogen is the smallest atom and forms the smallest molecule in nature. Therefore, hydrogen easily penetrates microscopic gaps in seals and even penetrates atomic lattices of metals. Thus, all known methods for storing hydrogen are heavy, and all are temporary, that is, they leak at appreciable rates.

The difficulty of storing hydrogen has been of concern to both NASA and the fuel cell community and has been a subject of research for decades. The issues of storage-system mass, volume and leak rates have been of primary concern even for terrestrial applications. No storage system offers a mass efficiency better than 20 percent; that is, 80 percent of the system weight consists of tankage or something other than hydrogen. At the same time, according to a recent NASA study, the minimum boil-off rate achievable with current technology is about 1.5 percent of hydrogen per day. On the basis of that estimate, the prospects for transporting hydrogen to Mars for oxygen and fuel production are negligible because the journey from Earth to Mars takes about 180 days.

Another known process for oxygen production accomplishes carbon dioxide conversion directly through solid-oxide electrolysis. The reaction takes place at high temperatures in a single stage according to the equation $$2CO_2 = 2CO + O_2.$$

No hydrogen or other consumables from Earth are needed to support this carbon dioxide conversion process; in addition, the carbon monoxide byproduct can also be used as a fuel.

Solid-oxide electrolysis is based on a discovery by Walther Nernst that certain ceramic oxides can conduct oxygen ions much as metals conduct electrons. This phenomenon, called "second conductivity" by Nernst, requires a high operating temperature for ionic conductivity to take place and is the principle underlying the use of solid oxides for fuel cell and electrolytic applications. Ionic conductivity is different from conduction of electrons in metals. Electrons in metals move relatively freely in electron clouds, whereas oxygen ions in a solid oxide hop between holes in the crystal lattice that are forced open by a dopant. A dopant is generally needed anyway to stabilize the crystal lattice against phase changes that would otherwise occur during heat up.

A typical solid oxide used in fuel cells and electrolyzers is cubic zirconia with yttria dopant ($Y_2O_3$), generally in a 8–10 percent yttria mole fraction. Yttria doped zirconia is known by the trade name "zircon" when used as artificial diamonds in costume jewelry. Fuel cells and electrolyzers employ the material in ceramic form, a polycrystalline agglomerate of randomly oriented crystals.

The properties of stabilized zirconia ceramics have been utilized in various fields of technology, from oxygen sensors for fuel-air ratio optimization of automobiles and furnaces; to solid-oxide fuel cells for noiseless and clean power generation from chemical energy; and oxygen pumps for solid state oxygen separation. The oxygen-ion conduction properties of stabilized zirconia used in typical oxygen sensor, fuel cell, or oxygen pump applications are well understood based on electrochemical-cell theory.

The polycrystalline solid-oxide electrolyte used in prior-art applications is formed into thin-sheet ceramics, either flat or of tubular geometry, with porous electrodes on both sides of the electrolyte. The role of the cathode in the oxygen-generation application of interest is to facilitate the division of $CO_2$ molecules into CO and O and to provide two electrons to each oxygen ion. The electrolyte allows the voltage difference across the electrodes to pump the oxygen ions toward the anode, and the anode accepts the electrons from the oxygen ions and permits them to combine into $O_2$ gas. The operation is efficient if surface and bulk resistivities are low, so that much of the voltage drop is invested in driving the chemistry. Typical system efficiencies of fuel cells are above 50 percent, and the same is achieved for solid oxide electrolysis.

Each oxygen ion within the electrolyte is doubly charged, so ionic current and oxygen production rate are directly related. An oxygen production rate of 0.1 kg/hr, for example, corresponds to an ionic current of 335 Amps. The potential needed to drive $CO_2$ electrolysis is about 0.8 Volts, and surface potentials add about 0.3 Volts per electrode. Thus, the minimum power needed to produce 0.1 kg of oxygen per hour is about 335×1.4=469 Watts. In practice, bulk resistivity of the electrolyte adds a bit to the power requirement, but bulk resistivity is low if the electrolytic sheets are thin and have a relatively large area.

Many solid-oxide cells have been developed for fuel-cell applications, such as zero-emission power sources for generators and vehicles. Solid-oxide electrolysis cells are essentially solid-oxide fuel cells with reversed polarity. In fact, solid-oxide electrolysis cells can be run as power generators by flowing air or oxygen on one side of the electrolyte and carbon monoxide on the other. Therefore, system-mass considerations and the knowledge already generated by industrial developments in the field provide good arguments in favor of solid-oxide electrolysis, rather than other known processes, as a means for producing oxygen on Mars.

While the polycrystalline ceramics used in prior-art solid-oxide applications provide the electrochemical vehicle for the electrolytic process for oxygen production, in practice they are not acceptable for extra-terrestrial applications, where physical strength and reliability during thermal stresses are essential. The solid-oxide electrolyte utilized for production of oxygen in Martian atmosphere must be capable of withstanding the shocks of transportation and the stresses caused by temperature cycles from the 900–1,000° C. operating temperatures during electrolysis to below zero ° C., the typical temperature to which equipment is subjected during Martian nights. Polycrystalline ceramics shrink and tend to crack under severe heat exposure. They cannot be machined to strict tolerances because of their porous structure and are too brittle for pressing to form a seal. Therefore, glues must be used to assemble the hermetic cells required for the electrolytic production of oxygen from $CO_2$. The resulting structures are relatively fragile and cannot be disassembled without totally disabling them. These problems, which are serious for commercial applications on Earth, appear insurmountable for extraterrestrial applications.

Therefore, there is still a need for a viable solid-oxide material for fuel-cell and electrolytic applications under harsh operating conditions. The present invention discloses a novel approach that satisfies these requirements for any application, and that is particularly suited for the cyclical production of oxygen from the carbon dioxide atmosphere of Mars.

SUMMARY OF THE INVENTION

One of the objectives of this invention is a solid-oxide electrolyte that is suitable for electrolytic and/or fuel-cell applications under severe mechanical and thermal stresses, such as encountered in space applications.

Another objective of the invention is an electrolyte material that can be machined to strict tolerances, such that it can be polished and used to form a seal by contact without a glue or other binding agent.

Another goal is an electrolyte material that can withstand the pressure required to form a contact seal without deformation or cracking that would damage the integrity of the seal.

Another objective is an electrolyte material that is capable of withstanding repeated thermal cycles between temperatures below 0 ° C. and about 1,000° C. free of damage from shrinkage and/or other thermal effects.

Yet another goal is a solid-oxide electrolyte with a coefficient of thermal expansion substantially equal to that of the electrode material utilized to fabricate the electrolytic cell or fuel cell in which it operates, such as to avoid shifts and dislocations caused by thermal stresses.

Still another objective is a method of electrolytic-cell or fuel-cell construction that affords flexibility of design, ease of repair, and efficient exploitation of the electrochemical properties of the solid-oxide electrolyte.

Finally, another goal is an electrolytic-cell or fuel-cell design that is suitable for stacking of electrolyte components to increase capacity without loss of efficiency.

Therefore, according to the foregoing objectives, the main aspect of this invention involves the use of a single-crystal solid oxide material, rather than a polycrystalline ceramic. Single-crystal materials are shock resistant, easily machinable to very precise tolerances, and readily available because used in large quantities by the electronic industry. According to another aspect of the invention, specific to the electrolytic production of oxygen from carbon dioxide, a yttria-stabilized zirconia crystal is coated with platinum electrodes and encased in a platinum structure to provide a thermally stable electrolytic cell. Because zirconia and platinum have substantially equal coefficients of thermal expansion, no significant thermal stresses occur during thermal cycling. According to yet another aspect of the invention, a multi-layered device is constructed by stacking crystals and spacers in alternating arrangement and by plumbing the active surfaces of the crystals in parallel through perforations drilled directly in the solid-oxide crystals, so that manifolding and sealing problems are minimized.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

DETAILED DESCRIPTION OF THE INVENTION

A primary aspect of this invention lies in the discovery that single-crystal oxides are suitable electrolytes for fuel-cell and electrolysis applications. All of the prior-art work on solid oxide fuel cells and electrolyzers has been based on Nernst's discovery that ionic conductivity takes place only in ceramics. That premise has an intuitive appeal, since ceramics are jumbles of crystals that might seem to afford some permeability. But it is now understood that oxygen ions do not diffuse through the oxide; rather, they hop from one lattice vacancy to another. Thus, it occurred to me that intercrystalline boundaries may restrict ionic conduction rather than enhance it and that a single solid-oxide crystal may offer not only greater robustness but also lower resistance.

Figure 1:
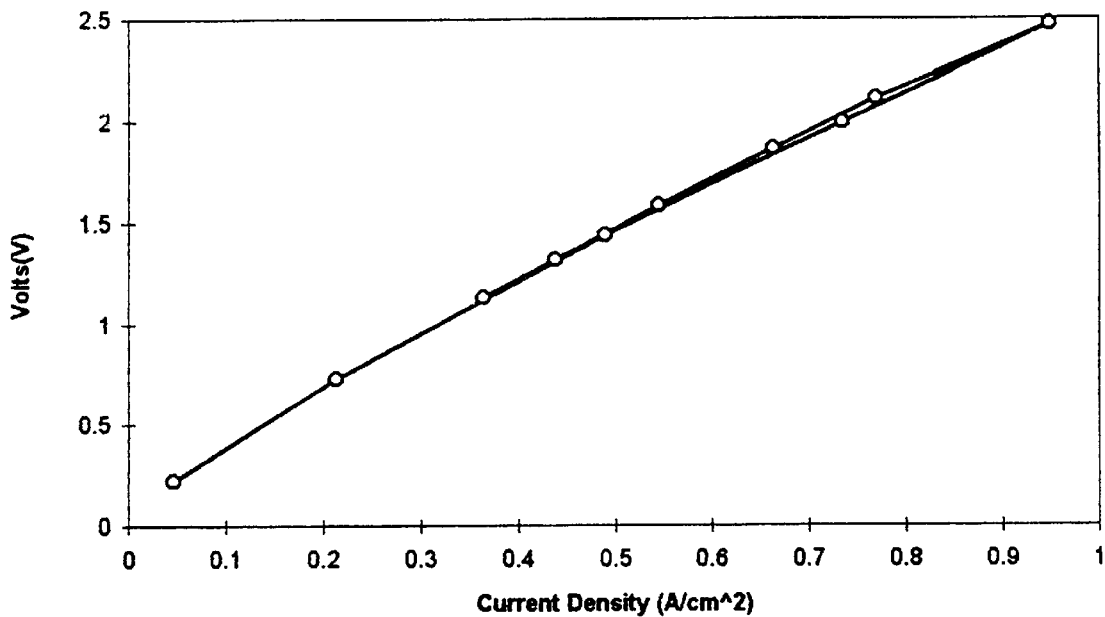
FIG. 1 is a voltage versus current density graph of single crystal zirconia in oxygen at one atmosphere and 950° C.

This hypothesis was confirmed experimentally by an oxygen pumping test on a single zirconia crystal with 9.5 mole percent $Y_2O_3$ dopant. The crystal used consisted of an impervious, clear, and strong disc 50 mm in diameter and 0.5 mm thick, plated on both sides with simple platinum electrodes. The cathode side of the disc was exposed to oxygen at one atmosphere and 950° C. and current densities were measured as a function of applied voltage. The maximum current density of almost 1 Amp/$cm^2$ obtained during the test was almost three times higher than obtained with zirconia in ceramic form. The results of the test are illustrated in FIG. 1, which shows some hysteresis effects from voltage cycling. The test confirmed the hypothesis that the resistance of single-crystal zirconia is reasonably low and almost certainly can be reduced with more sophisticated electrodes.

Single crystal zirconia wafers are shock resistant, quite unlike the rather delicate ceramics that have been used in the past. Moreover, zirconia wafers are readily available and inexpensive because they are used as substrates for solid state electronic devices. Thus, any electrolytic or fuel-cell device build with single-crystal solid oxide would be a true solid state device; in the case of single-crystal zirconia wafers, the device would have strength characteristics comparable to those of diamonds.

Based on this discovery and the attendant advantages, I investigated the use of single-crystal solid-oxide electrolyte material for fuel-cell and electrolytic applications, such as the space mission contemplated for Mars. The ultimate operating conditions of the mission guided the selection of parameters for the research tests. The version of an oxygen-producing device required for a Mars mission would produce about 1 kg of $O_2$ during 10 hours of daylight, or 0.1 kg of $O_2$ per hour. The equivalent ionic current is 335 A. By stacking multiple single-crystal elements and wiring the cell in series, the current across the device can be reduces by a corresponding factor (such as 20 for a 20-layer stack).

Application of the first law of thermodynamics to $CO_2$ electrolysis indicates that at least 490 W is needed to produce 0.1 kg of $O_2$ per hour. Of the total power, 280 W must be electric power; the rest must be heat, because the reaction is endothermic. The crystal cells could be run at 280 W and the heat could be provided with auxiliary heaters, but a better option is to use the crystal themselves as resistive heaters. Run that way, the potential drop across each crystal (each cell) would be 1.46 V (i.e., 490 W divided by 335 A). The actual voltage needs to be a little higher to compensate for heat losses. A good target is 1.6 V across each crystal, so a specific objective of the tests that underlied this invention was to confirm high $CO_2$ conversion efficiency at 1.6 V.

Figure 2:
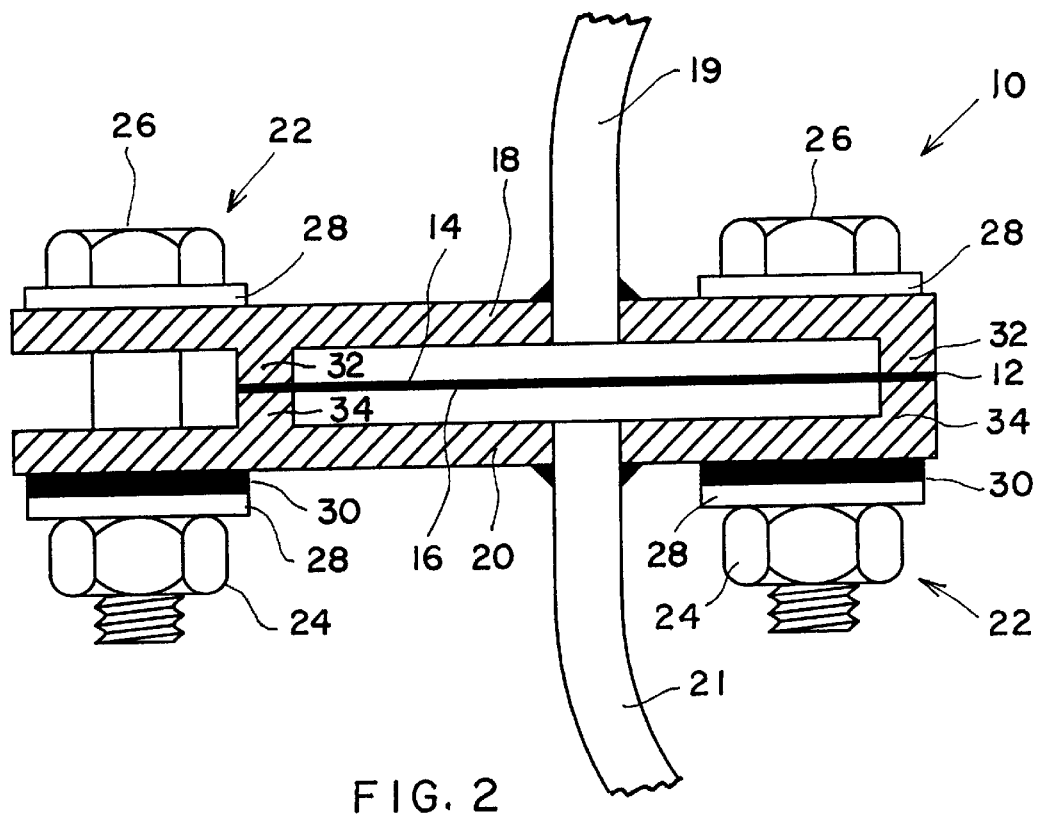
FIG. 2 is a schematic illustration of a single-crystal cell according to the invention.

FIG. 2 illustrates a single-crystal test cell 10 according to the invention as utilized in the experiments. The electrolyte consisted of a single crystal 12 of yttria stabilized zirconia (8 mole %), 50 mm in diameter and 0.5 mm thick. The electrodes 14 and 16 (referenced in the figure but not distinctly shown because too thin to be visible in scale) consisted of platinum silk-screened uniformly onto both sides of the zirconia disk. This process is well known in the art and performed, for example, by the Cermalloy Division of Heraeus, Inc., of W. Conshohocken, Pa. After encapsulation of the coated crystal between the end caps 18 and 20, the resulting active area of each electrode within the cell was about 13.85 $cm^2$. The crystal disk 12 was machined and polished to very fine tolerances to provide a nearly-perfect flat surface suitable for forming a hermetic seal by contact with conforming surfaces in the end caps of the cell. Flow tubes 19 and 21 attached (such as by welding) to the end caps 18 and 20, respectively, provided hermetic inlet and outlet ports for the cell's feed and product. The end caps 18,20 and the corresponding flow tubes 19,21 were made of platinum to withstand high temperatures and to match the thermal expansion coefficient of zirconia, thereby minimizing thermal stresses during heating and cooling cycles. Bimetallic fasteners 22 secured the end caps. Each fastener consisted of a nut 24, a bolt 26, and washers 28 made of the nickel alloy Inconel®, and of a spacer 30 made of the nickel alloy Haynes®. This combination of alloys was selected because it can be arranged to match the thermal expansion of the zirconia and platinum components, thereby further minimizing thermal stresses. As would be obvious to one skilled in the art, the specific size of the Haynes spacer 30 can be chosen to complement the geometry of the Inconel components of the fastener 22 to match the thermal expansion characteristics of zirconia and platinum.

The variables under control in the test cell 10 were $CO_2$ mass flow rate, temperature, and voltage. The pressures on both sides of the cell were controlled by downstream conditions, and were set at one atmosphere for the tests reported here.

The behavior of the electrolytic cell shown in FIG. 2 was first modeled based on solid-oxide electrolytic theory assuming that CO and $CO_2$ are well mixed in the plenum on their side of the cell. The theory also assumes conservation of atoms, downstream pressure matching, thermodynamic equilibrium in the CO/$CO_2$ plenum, conservation of enthalpy, and conservation of entropy with Ohmic resistance as an entropy source. The theory uses an area utilization factor representing the radial decrease of the applied voltage inward from the platinum rings 32 and 34 (FIG. 2) that serve as electrical contacts and cell walls. The area factor can be calculated exactly from the electrode thickness, but it was set at 0.4 for the tests reported here, a reasonable value for the cell's geometry.

Figure 3:
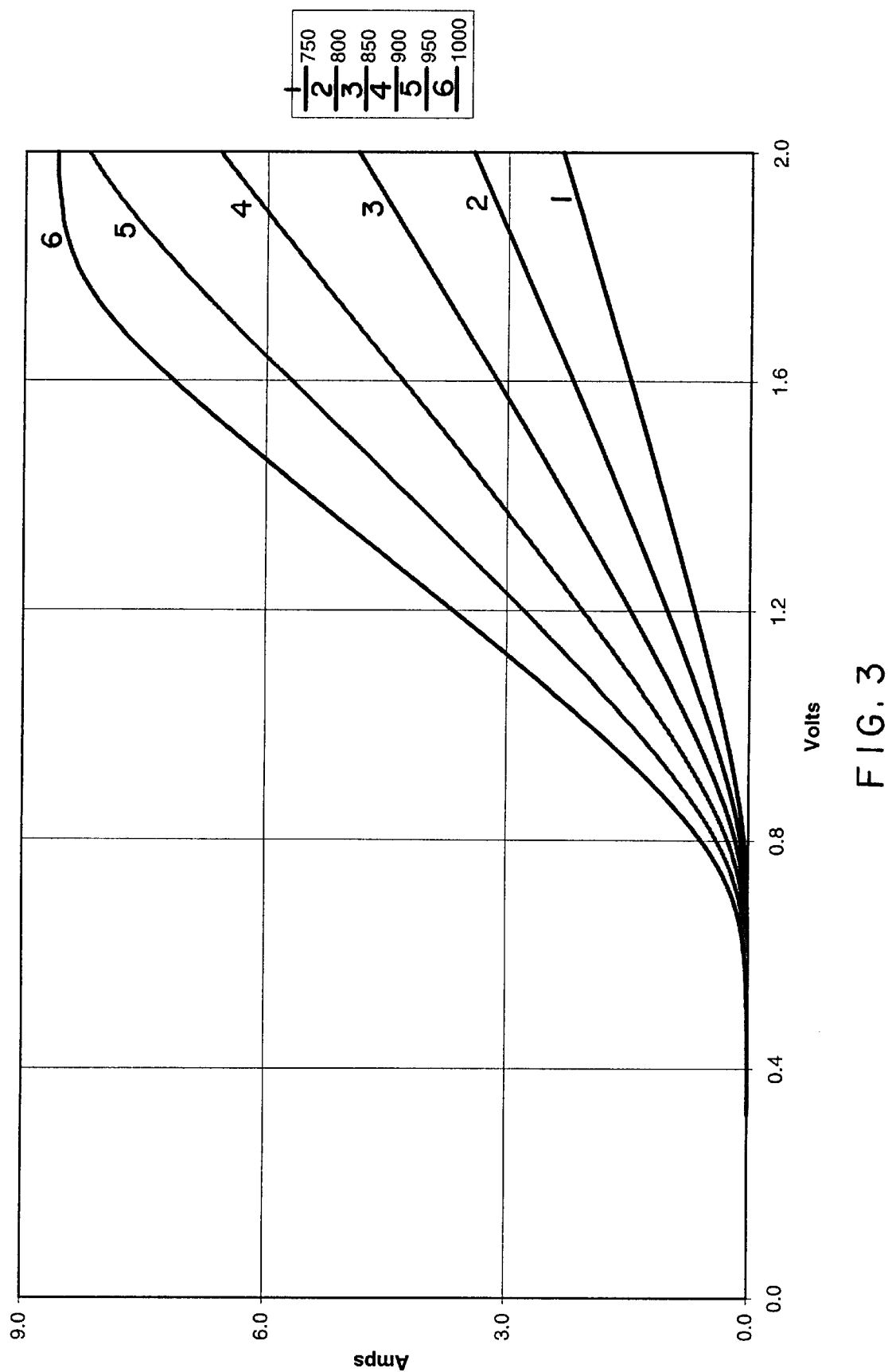
FIG. 3 shows theoretical voltage-versus-current graphs of single-crystal zirconia performance at various temperatures with a $CO_2$ feed rate of 60 cc/min.

FIG. 3 shows the theoretical (calculated) performance of the cell 10 for a $CO_2$ flow rate of 60 cc/min (measured at standard pressure and temperature). The ionic current through the cell, proportional to $O_2$ production rate, is shown as a function of applied voltage. If all the $CO_2$ were converted to CO, the ionic current would be 8.6 A. The six curves in the plot pertain to temperatures ranging from 750 to 1,000° C. in steps of 50 degrees. Since current increases with temperature, the lower curves correspond to lower temperatures. The plot shows that the current is negligible below 0.8 V, then rises more or less linearly with voltage until it comes close to the limit of 8.6 A, where $CO_2$ conversion would be 100%.

Note that, as stated above, a goal of the project was to convert $CO_2$ efficiently at 1.6 V. Based on FIG. 3, at 1,000° C. and 1.6 V the theory indicates that the cell 10 would convert 83% of the $CO_2$ input to CO, but the conversion efficiency decreases rapidly with decreasing temperature. At 900° C. and 1.6 V, the conversion efficiency is only 50%.

Figure 4:
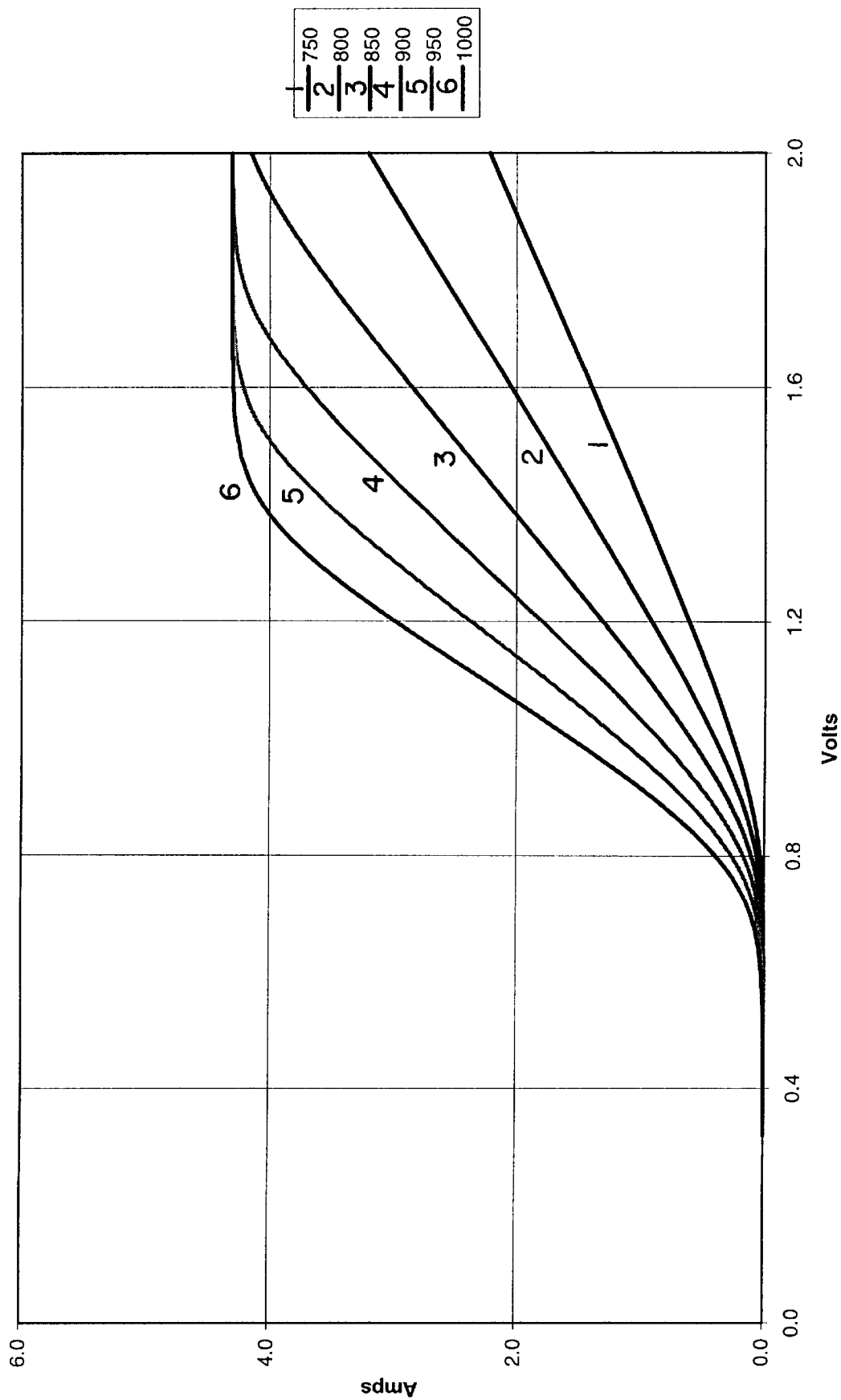
FIG. 4 shows theoretical voltage-versus-current graphs of single-crystal zirconia performance at various temperatures with a $CO_2$ feed rate of 30 cc/min.

FIG. 4 shows the results of calculations based on a reduced $CO_2$ flow rate of 30 cc/min, for which the maximum ionic current is 4.3 A. The upper limit imposed by $CO_2$ flow is much more apparent in this case, indicating that high conversion efficiencies are possible at reduced temperatures. For example, at 900° C. and 1.6 V, the theoretical conversion efficiency is 86%. Of course, the current density is lower at 900° C. than at 1,000° C., but FIG. 4 suggests that high $CO_2$ conversion efficiencies are possible at reduced temperature. The current density at 900° C. and 1.6 V is about 0.27 A/cm2, an acceptable value for the cell of the invention. At that operating point, the device of the invention would need about 22 disks, each about 4 inches in diameter, to accomplish the task desired for the Martian mission. These parameters are perfectly tolerable to produce an assembly suitable for extraterrestrial applications.

Figure 5:
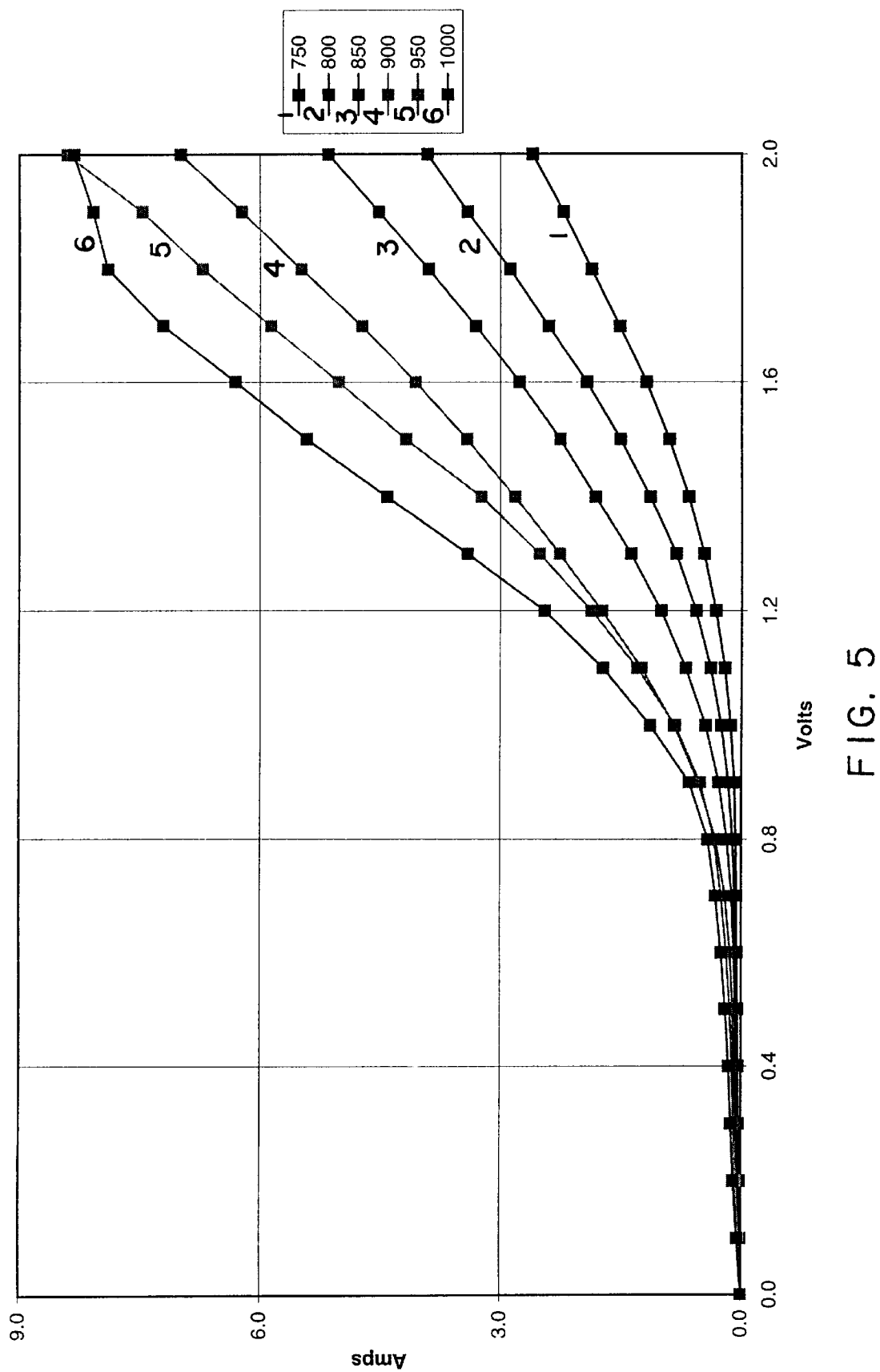
FIG. 5 shows experimental voltage-versus-current graphs of single-crystal zirconia performance at various temperatures with a $CO_2$ feed rate of 60 cc/min.
Figure 6:
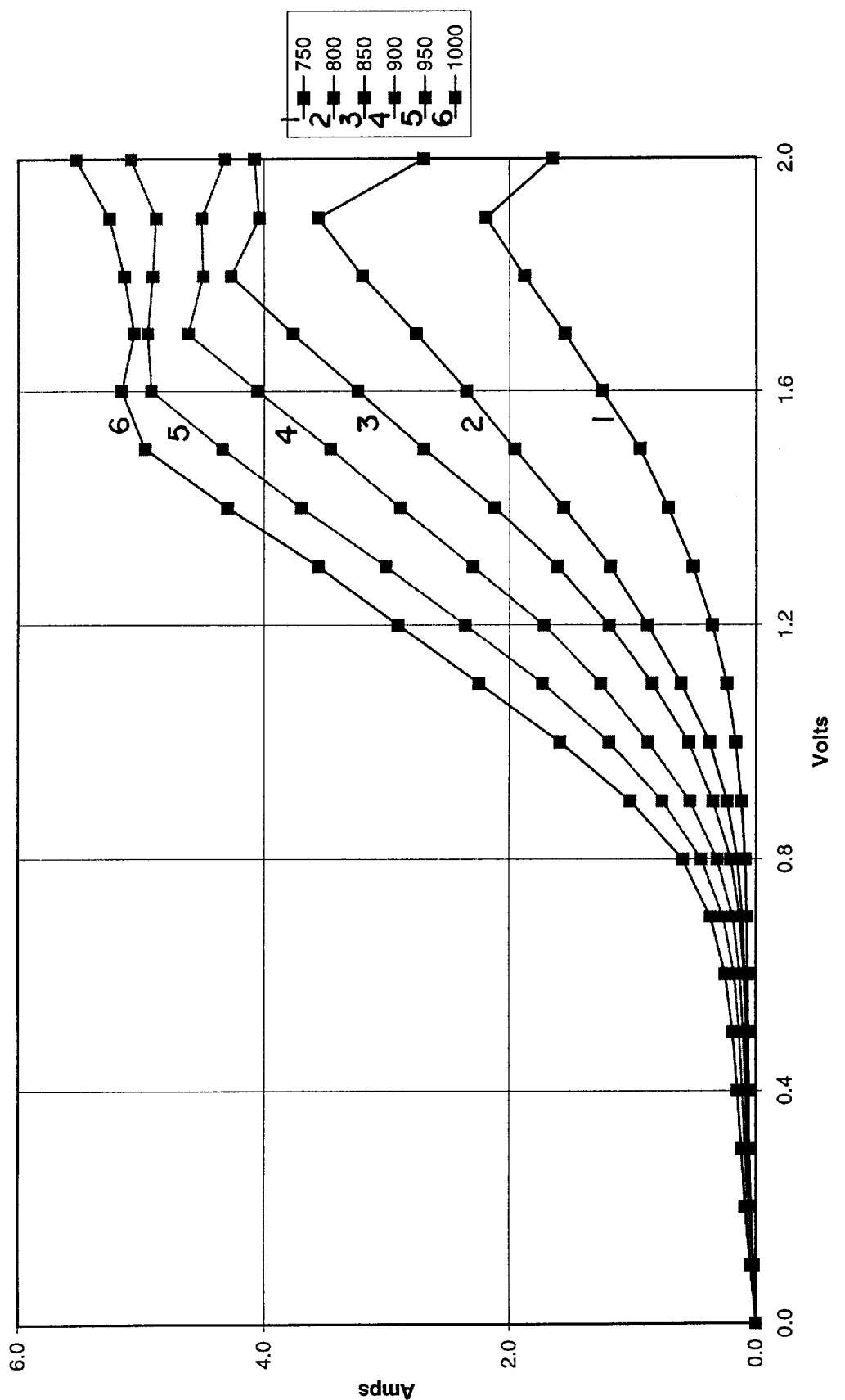
FIG. 6 shows experimental voltage-versus-current graphs of single-crystal zirconia performance at various temperatures with a $CO_2$ feed rate of 30 cc/min.

FIGS. 5 and 6 show actual test data for the cell 10 at $CO_2$ flow rates of 60 and 30 cc/min, respectively. A mass flow valve controlled the flow rates, which were further validated by bubbling the $CO_2$ into an inverted flask filled with water. FIGS. 5 and 6 can be compared favorably with the theoretical plots of FIGS. 3 and 4, demonstrating that the theory clearly captures a large part of the phenomenology of solid-oxide electrolysis.

The comparisons reveal some anomalies, however, especially at the lower $CO_2$ flow rate of 30 cc/min. At that flow rate and at lower temperatures, the current actually decreases as voltage increases from about 1.8 or 1.9 to 2.0 V. The decrease is reproducible and real and, even more unsettling, the current is higher than the upper theoretical limit of 4.3 A at the higher voltages and temperatures. In fact, this excess ionic current is believed to be an edge effect, caused by exposure of the zirconia disk to air. The exposure is evident from the illustration in FIG. 2 and takes place along the disk perimeter sandwiched between the end-cap rings 32 and 34. The perimeter has an area of about 0.79 cm², a significant fraction of the active area of the disk faces within the cell. The edge, moreover, is exposed to $O_2$ which supports a much higher current density than $CO_2$ conversion at the same temperature and voltage. Moreover, the edge sustains the full potential difference across the platinum end caps, while the electrodes inside the cell suffer an attenuation of potential difference due to the radial electronic current.

Figure 7:
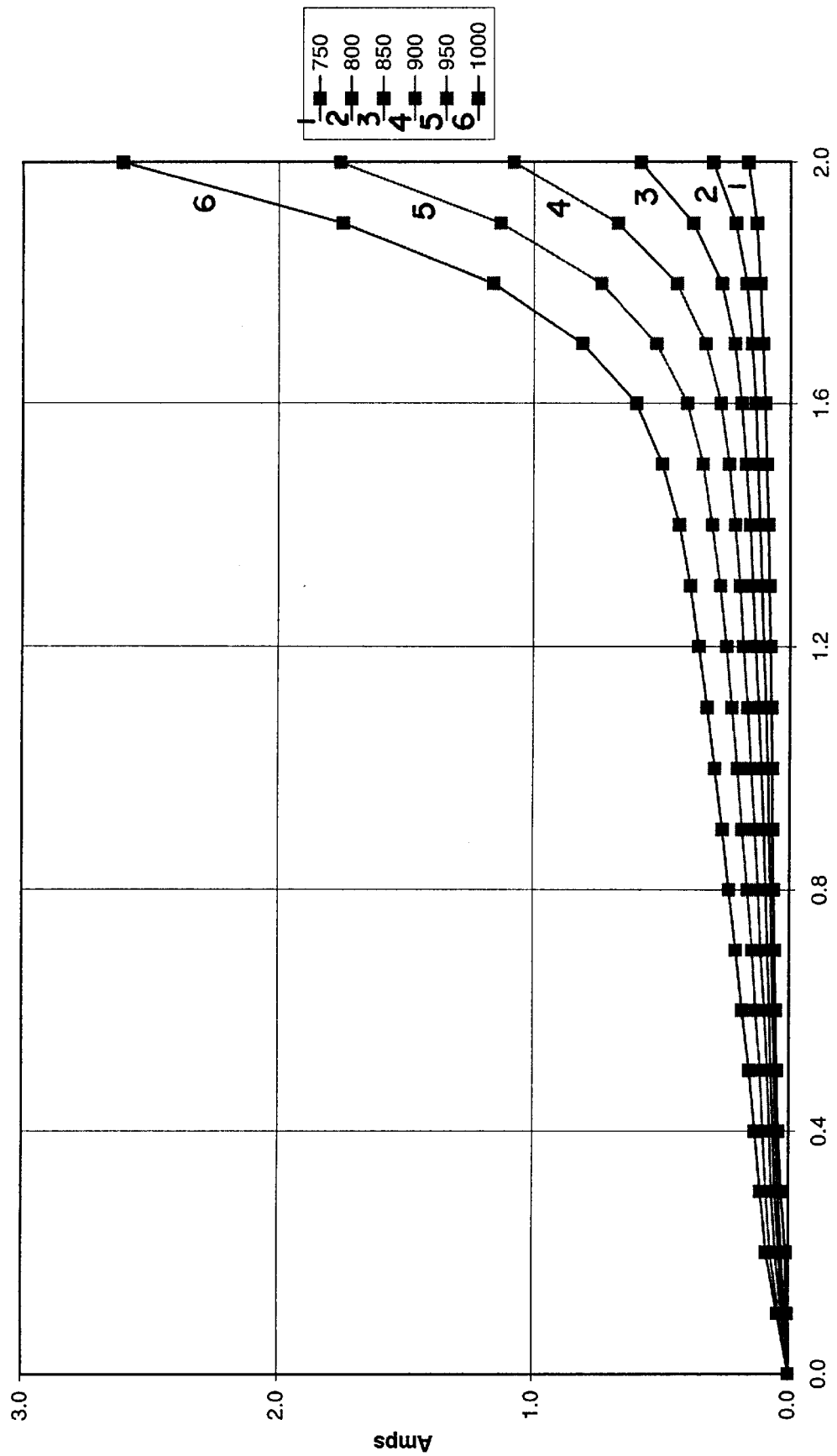
FIG. 7 shows experimental voltage-versus-current graphs of single-crystal zirconia performance at various temperatures with an argon feed rate of 60 cc/min.

An edge correction can be determined by replacing the $CO_2$ inflow with argon, which provides no oxygen ions for conduction within the cell. FIG. 7 shows the results of tests with Ar as the input gas, flowing at a rate of 60 cc/min referenced to standard pressure and temperature. The plot has the same format as FIG. 6, but is amplified by a factor of two along the current axis. The data show that the edge current increases with temperature and increases linearly with voltage up to about 1.2 V. No threshold at 0.8 V is evident, and no oxygen flowed within the cell, as confirmed by the lack of production of bubbles in an inverted flask at the outlet.

This test shows that the disk edge correction exhibits its own anomaly at higher voltages and temperatures. The current seems to rise exponentially with voltage. Indeed the current seemed to diverge slowly with time at the more elevated voltages and temperatures, as though the cell were slowly heating. Although unexplained, this current anomaly in the argon tests was also found to be real and reproducible.

Figure 8:
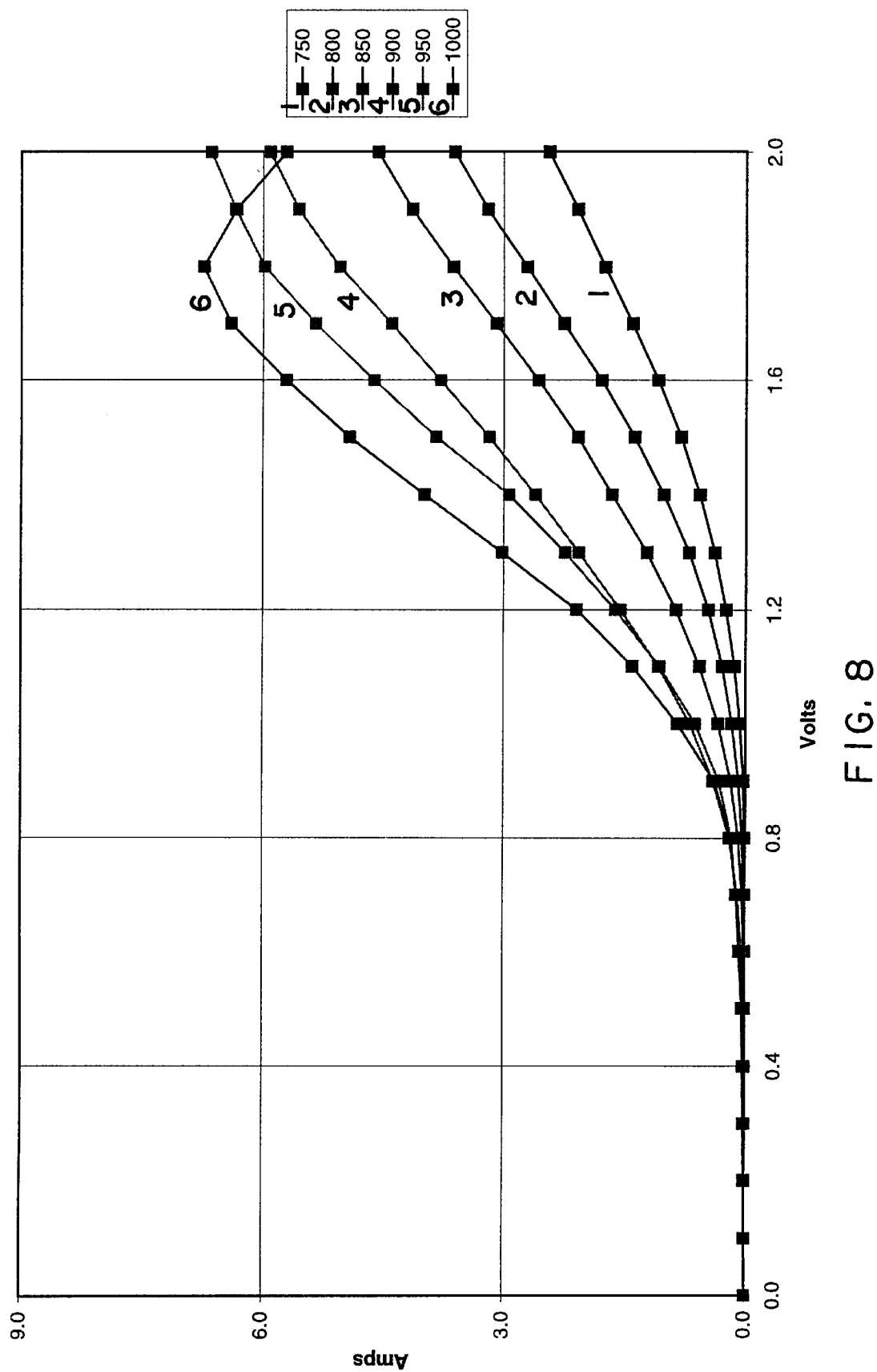
FIG. 8 shows corrected experimental voltage-versus-current graphs of single-crystal zirconia performance at various temperatures with a $CO_2$ feed rate of 60 cc/min.
Figure 9:
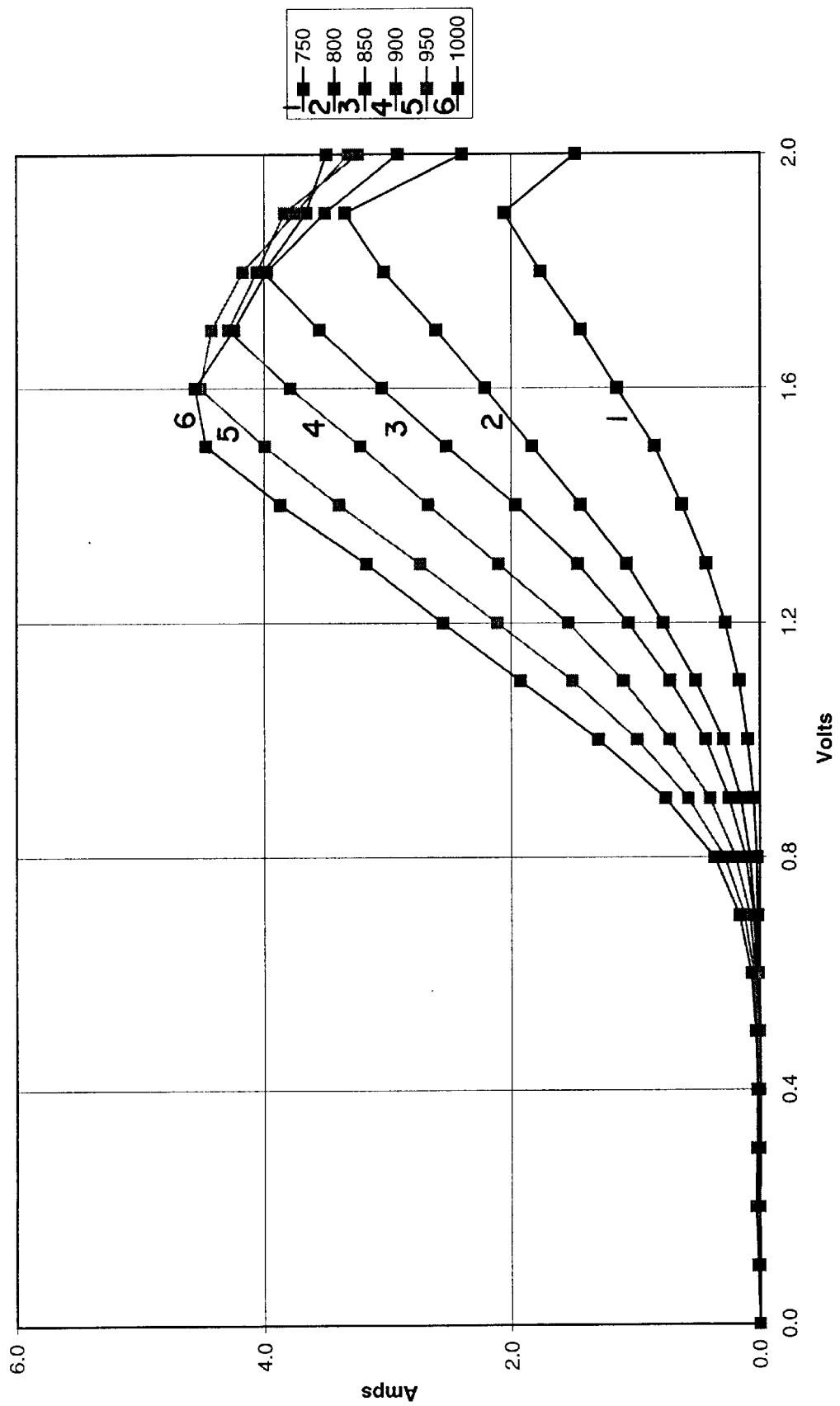
FIG. 9 shows corrected experimental voltage-versus-current graphs of single-crystal zirconia performance at various temperatures with a $CO_2$ feed rate of 30 cc/min.

FIGS. 8 and 9 show the result of subtracting the presumed edge current of FIG. 7 from the total currents displayed in FIGS. 5 and 6. The correction is modest below 1.6 V, but produces strange behavior at higher voltages, reflecting an apparent reduction of ionic current with increasing voltage. The linear portions of the curves in FIG. 7 almost certainly reflect oxygen ion pumping around the periphery of the disk exposed to air. On the other hand, the cause of the exponential current at the higher temperatures and voltages is not clear. Previous tests have shown a linear relation between current and voltage when oxygen is the feed gas. Therefore, it is believed that the exponential part of the current may not be ionic at all, but some sort of electron conduction across the zirconia disk.

Figure 10:
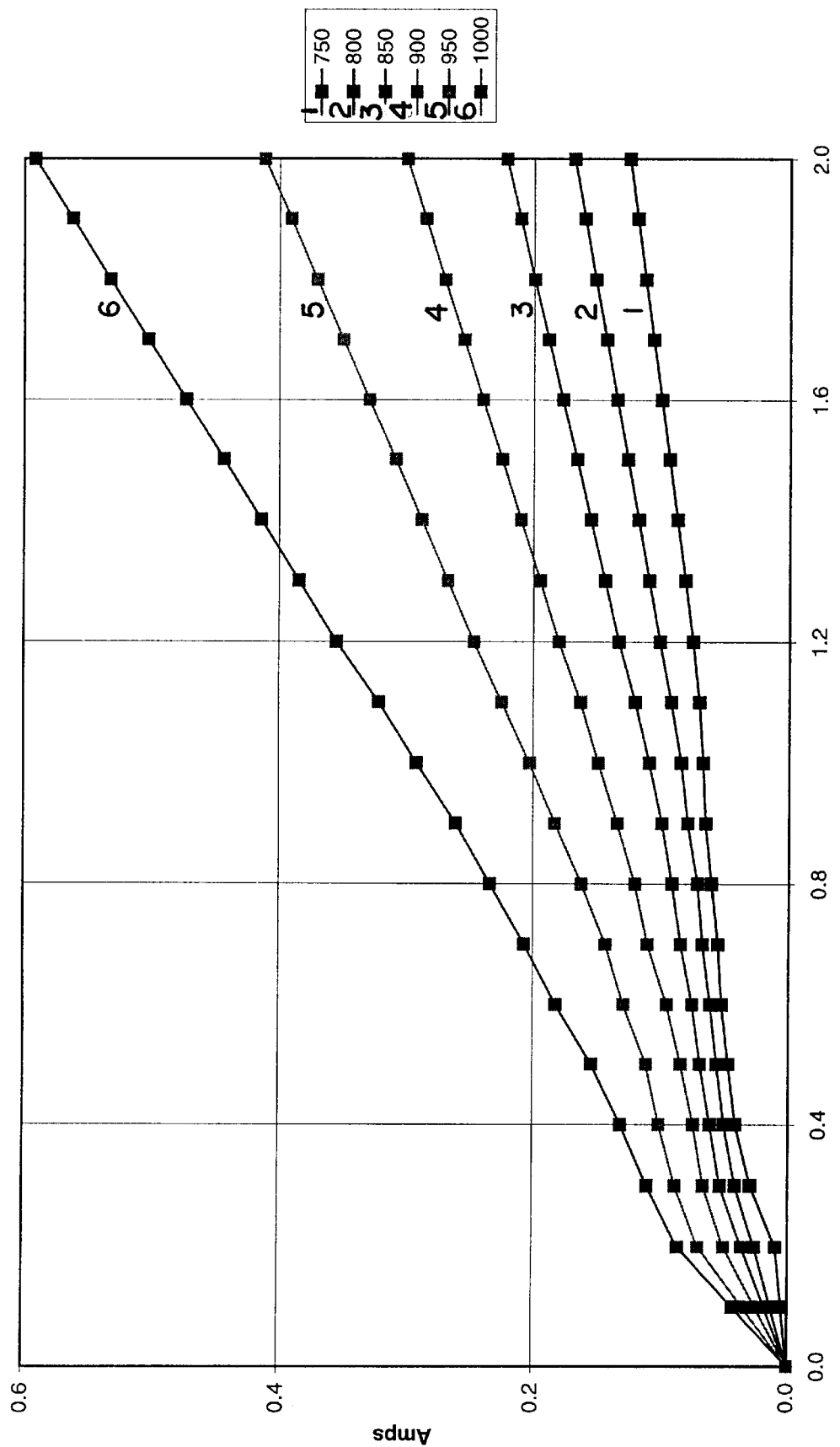
FIG. 10 shows experimental voltage-versus-current graphs of single-crystal zirconia performance at various temperatures with an argon feed rate of 60 cc/min, with linear extrapolation of the data beyond 1.2 Volts.

In any event, the exponential parts of the edge corrections produced most unlikely results when subtracted from the currents measured with $CO_2$ as the feed gas. Therefore, a modified-correction approach was followed based on the assumption that the phenomenon simply does not occur when $CO_2$ is present to provide oxygen ions for transport through the electrolyte. FIG. 10 reflects that approach by extrapolating the edge correction linearly from 1.2 to 2.0 V, without regard for the exponential nature of the current actually measured with Ar.

Figure 11:
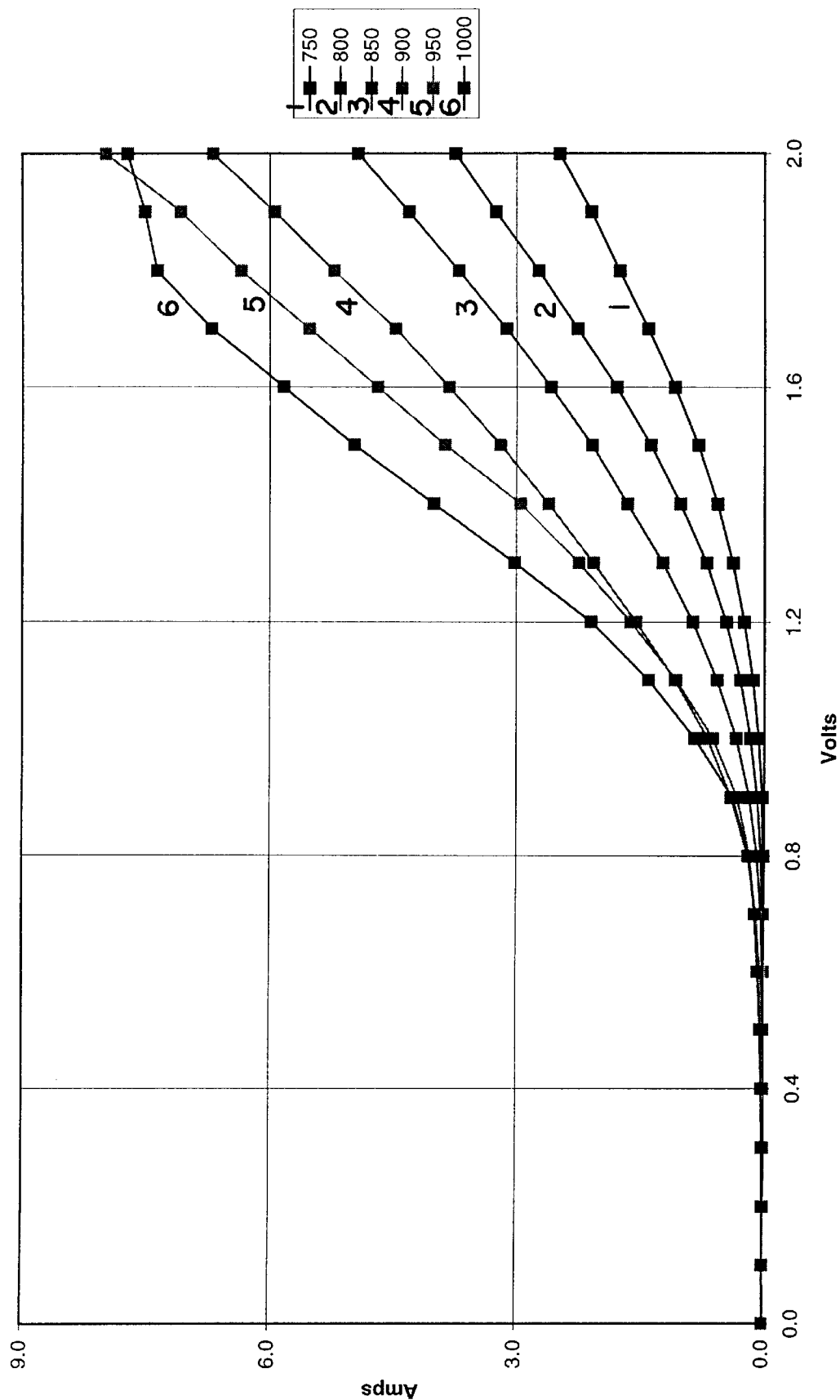
FIG. 11 shows experimental voltage-versus-current graphs of single-crystal zirconia performance at various temperatures with a $CO_2$ feed rate of 60 cc/min, with modified corrections based on the data of FIG. 10.
Figure 12:
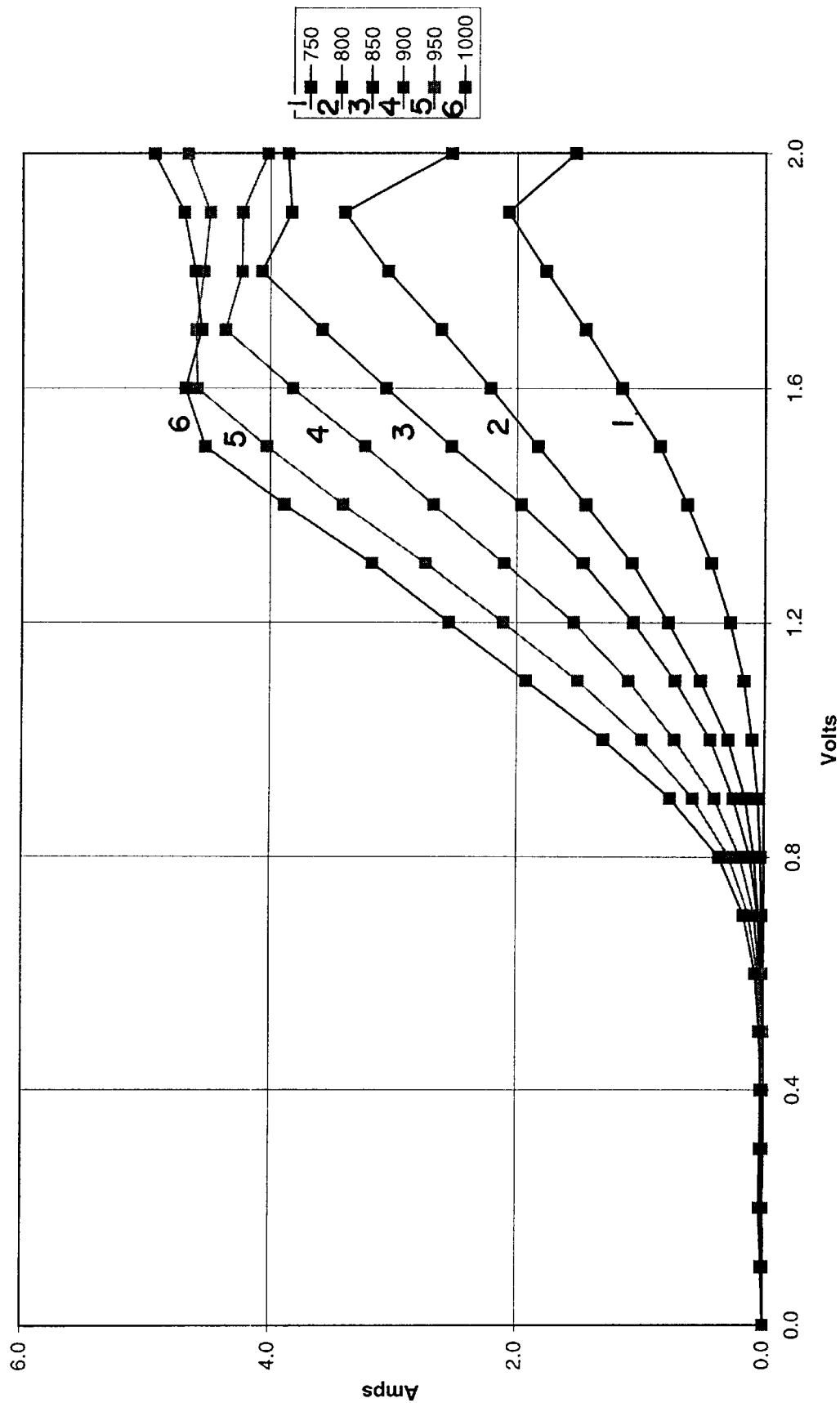
FIG. 12 shows experimental voltage-versus-current graphs of single-crystal zirconia performance at various temperatures with a $CO_2$ feed rate of 30 cc/min, with modified corrections based on the data of FIG. 10.

FIGS. 11 and 12 show the results of applying the modified corrections of FIG. 10 to the data of FIGS. 5 and 6. According to FIG. 11, the highest conversion efficiency was 93% at a $CO_2$ flow rate of 60 cc/min. The peak conversion rate occurred at a temperature of 950° C. and a voltage of 2.0 V. At the target voltage of 1.6 V, the highest conversion efficiency was only 68%, realized at 1,000° C. Because of the uncertainties associated with high voltages, it is believed that it would be unwise to operate an extraterrestrial device at 2.0 V. It would also be uneconomical because excess power would be needed and the excess heat would have to be removed from the cell. Therefore, the conclusion is that a $CO_2$ flow rate of 60 cc/min would be too large for the device of the invention operating under the prescribed conditions.

A $CO_2$ flow rate of 30 cc/min offers a much better selection of options. At 1.6 V and 900° C., the conversion efficiency shown in FIG. 12 is about 89%. Even with the unmodified edge corrections of FIG. 9, the conversion efficiency at 1.6 V and 900° C. was 88%. Therefore, whatever the unexplained phenomenon is that occurs at higher voltages and temperatures, it does not have much effect at 1.6 V and 900° C.

These considerations imply the following specific operating conditions for the solid oxide (stabilized zirconia)

system of the invention: an approximate temperature of 900° C., a voltage across each crystal of about 1.6 volts, and a $CO_2$ flow rate of about 2.8 cc/min per $cm^2$ of active electrode area. Based on these criteria, it is expected that the $CO_2$ conversion efficiency would be around 89%, and the power required to produce 0.1 kg of $O_2$ per hour would be about 536 W. To produce $O_2$ at that rate, the required total active electrode area would be 980 $cm^2$. Twenty zirconia disks (each about 4 inches in diameter) wired in series would deliver $O_2$ at the desired rate.

These tests and conclusions pertain to an internal pressure of 1 atm on both sides of the crystal in each cell compartment. As long as the $CO_2$ mass flows remain the same, there is no theoretical reason to believe that reduced pressure would have much effect on the performance of the device. The theory indicates only minuscule changes in ionic current, and both molecular and turbulent diffusivities scale inversely with pressure.

On the basis of these test results, I endeavored to develop a single-crystal electrolytic cell for the production of oxygen in the Martian atmosphere in accordance with the following specifications:

1. Feed gas of $CO_2$ at 8 millibars pressure and a volume flow rate of about 50 liters per minute.
2. Product gas of $O_2$ at a pressure of at least 1 Earth atmosphere and a flow rate of 0.1 kg/hr. An output pressure of 42 atmospheres would be very desirable for liquefaction purposes.
3. Product leak rates of no more than 10 percent, with 1 percent being a preferred goal.
4. Operating temperature no more than 1,000° C., preferably as low as possible.
5. Cell resistance no more than 0.001 Ohms at the operating temperature with one atmosphere of $O_2$ on both sides of the electrolytes.
6. No more than 1,000 $cm^2$ of active electrode area. The cell should be as small and light as possible.
7. The cell must be able to survive at least 100 thermal cycles, each cycle consisting of 2 hours of heat up, 10 hours of oxygen production, and 12 hours of cool down with electric power and gas flows turned off.

Figure 13:
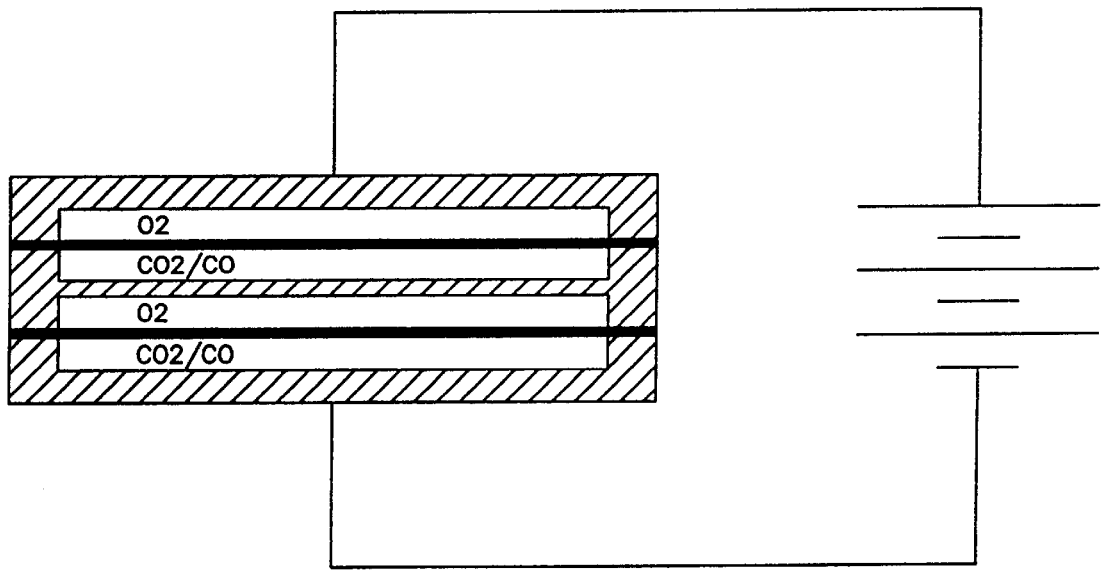
FIG. 13 is a schematic illustration of a two-cell device wired in series according to the invention.
Figure 14:
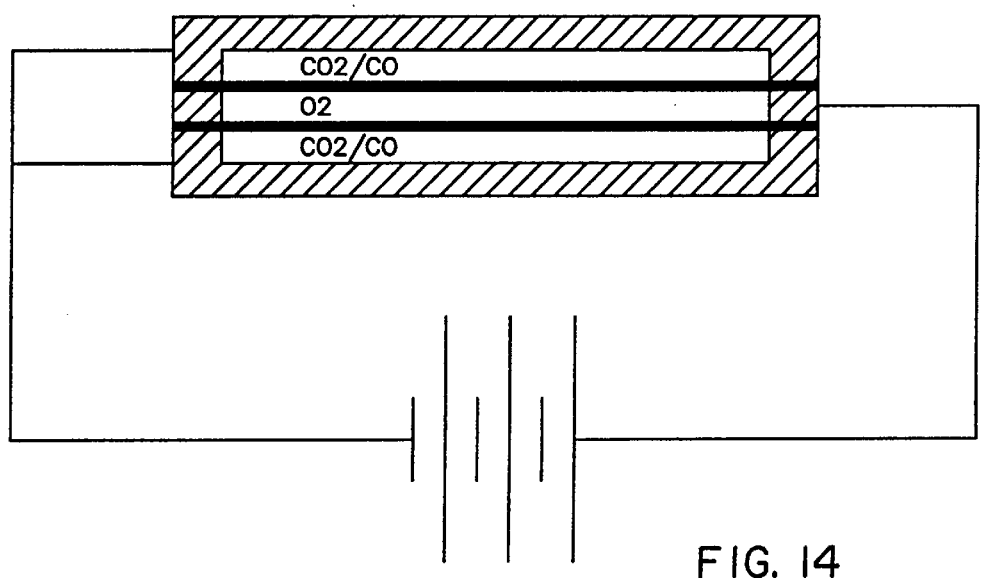
FIG. 14 is a schematic illustration of a two-cell device wired in parallel according to the invention.

Past work on solid-oxide electrolysis has focused on electrochemistry, with no special emphasis on the volume or weight of the cells. Tubular electrolytes and small ceramic discs have been used. The present invention is based on the use of monolithic solid-oxide crystals disposed in a layered-cell arrangement with interconnects that serve as conductors and flow conduits. FIGS. 13 and 14 illustrate such a multiple-cell approach wired in series and parallel, respectively. As indicated above, series is greatly preferred to reduce the current through the device.

Figure 15:
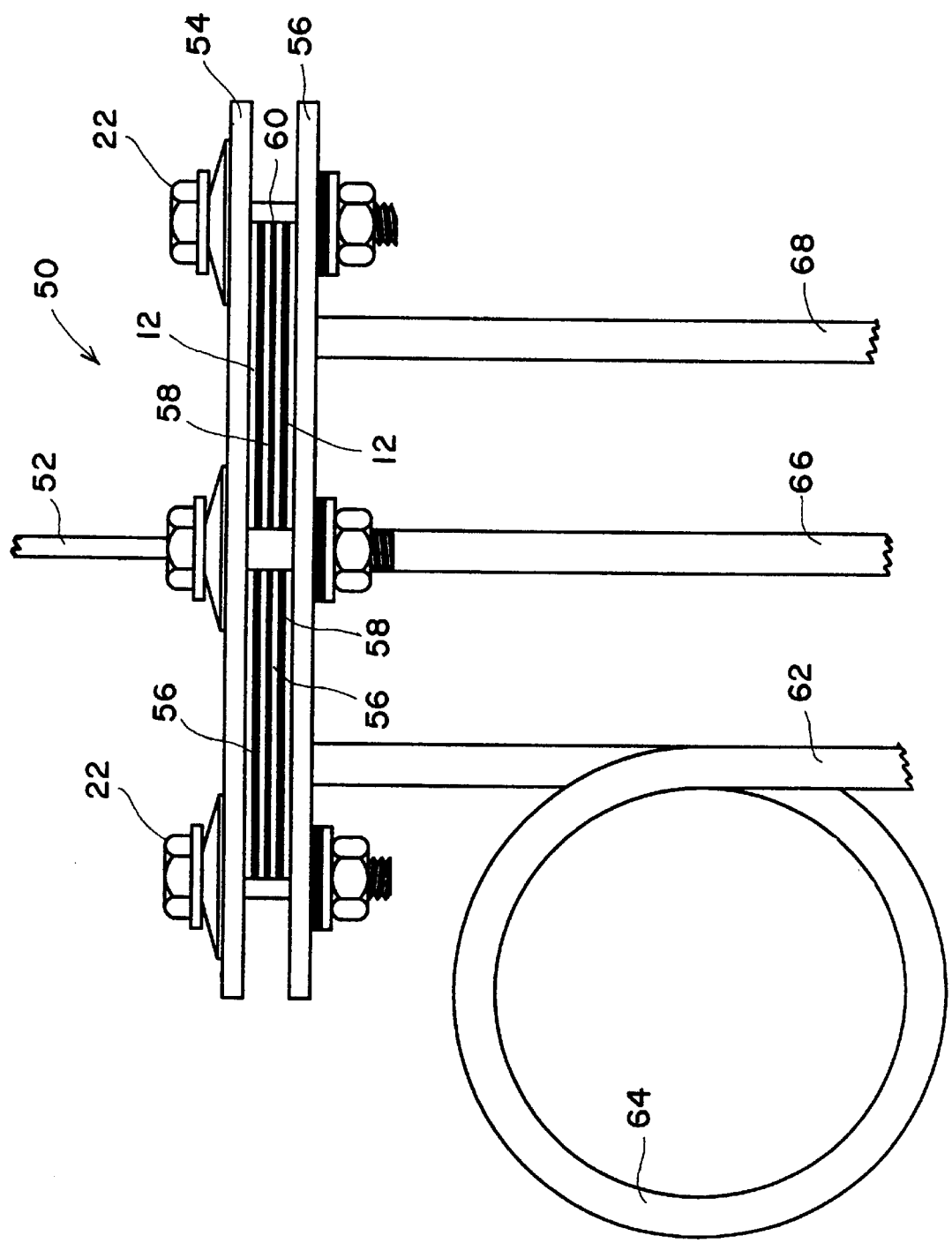
FIG. 15 is an elevational view of a two-cell electrolytic device according to the preferred embodiment of the invention.
Figure 16:
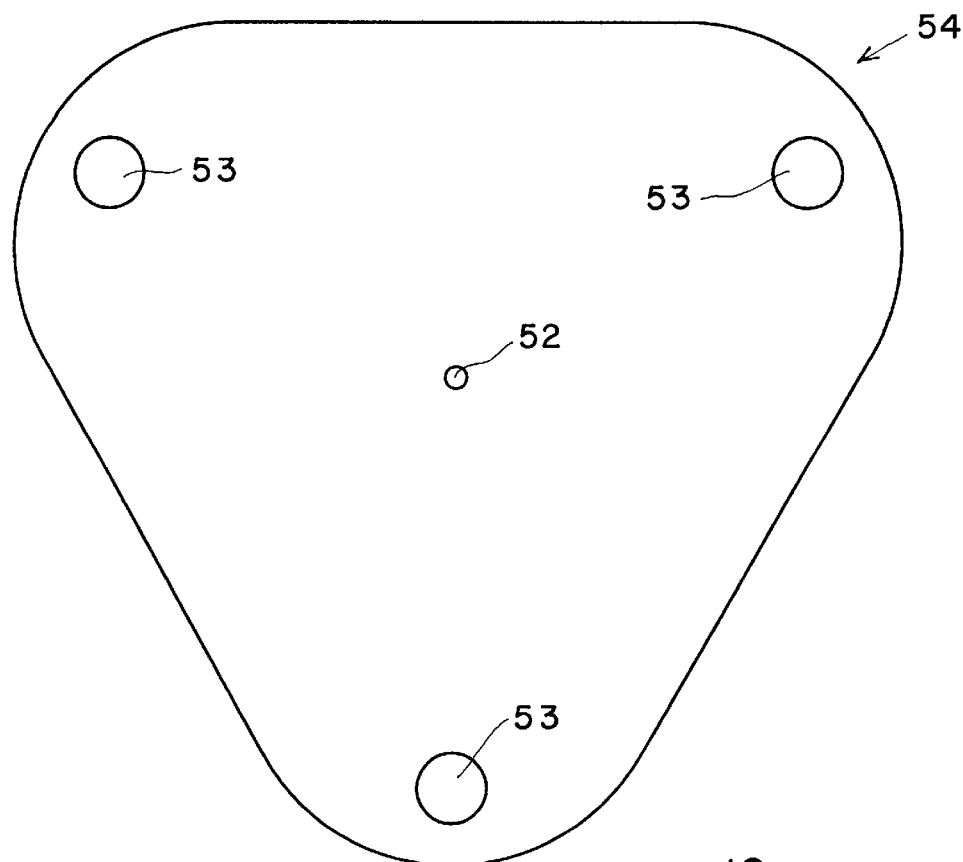
FIG. 16 is a plan view of the top plate in FIG. 15.

Referring to FIG. 15, a two-cell electrolytic device 50 according to the invention is illustrated in elevational view. Two discs, each consisting of a single stabilized zirconia crystal 12 coated with platinum electrodes, are stacked axially with alternating spacers to form two electrolytic cells connected in series (such as to form a pile). A ⅛th-inch platinum alloy rod 54 attached to an anodic top plate 54 serves as a live voltage contact, while three flow tubes attached to a cathodic bottom plate 56, are electrically grounded. Three bimetallic fasteners 22 of the type described in FIG. 2 are used to engage the plates 54,56 through matching holes 53 (FIGS. 16 and 21) and press them against alternating discs and spacers to form a hermetic closure.

Figure 21:
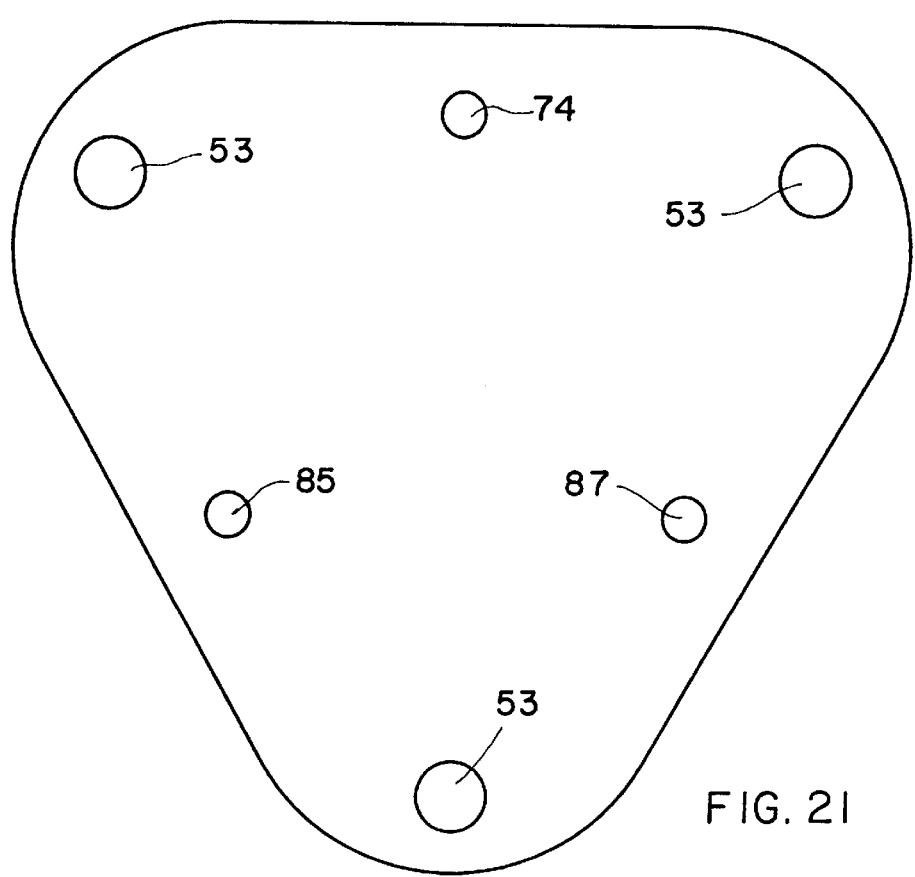
FIG. 21 is a plan view of the bottom plate in FIG. 15.

According to a novel approach afforded by the use of single-crystal structures instead of ceramics, the robust crystals 12 of the invention are perforated at three locations to provide flow channels that permit the elimination of exterior plumbing to feed and exhaust the stack of solid-oxide cells. FIGS. 16 to 21 illustrate the components of the stack. They are presented from top to bottom with reference to FIG. 15, though the stack can obviously be oriented as desired for use. The stack components consists of a top plate 54 (FIG. 16), made of ⅛th-inch platinum alloy plate; an oxygen grille 56 (FIG. 17) of the same alloy, about 2 inches in diameter and 0.050 inch thick; a zirconia disk 12 (FIG. 18), 50 mm in diameter, 0.5 mm thick, and coated on both sides with a silk-screened layer of platinum; a $CO/CO_2$ grille 58 (FIG. 19), about 2 inches in diameter and 0.050 inch thick; a diaphragm 60 (FIG. 20) made of 1/32nd-inch platinum alloy sheet; another oxygen grille 56; another zirconia disk 12; another $CO/CO_2$ grille 58; and a bottom plate 56 (FIG. 21). An inlet pipe 62 is provided for feeding $CO_2$ to the unit; a coiled portion 64 is used to increase residence time and preheat the feed. Outlet pipes 66 and 68 are used, respectively, to exhaust CO from the cathodic side and $O_2$ from the anodic side of each cell.

Figure 17:
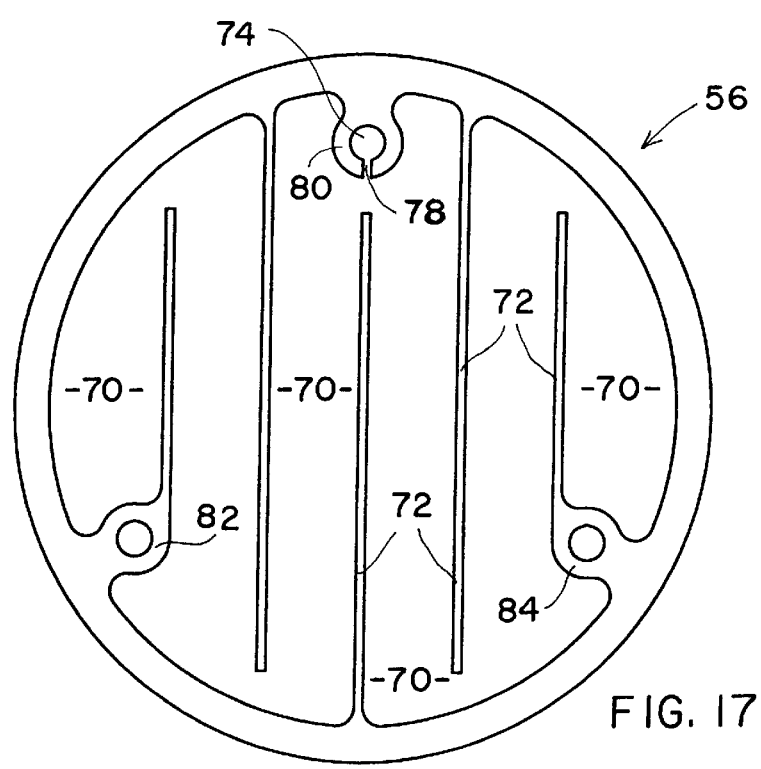
FIG. 17 is a plan view of the oxygen grille in FIG. 15.
Figure 18:
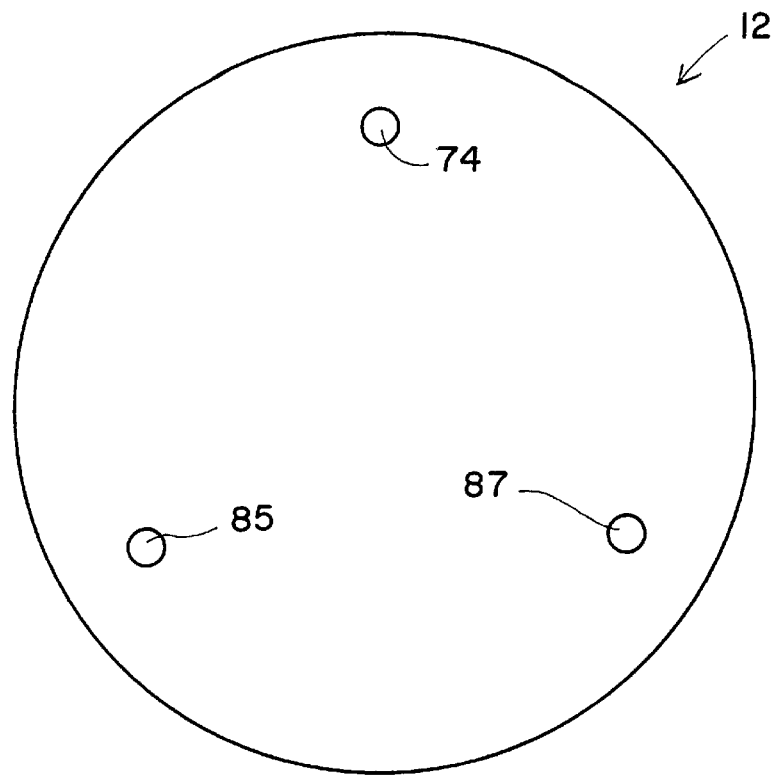
FIG. 18 is a plan view of the zirconia disk in FIG. 15.
Figure 19:
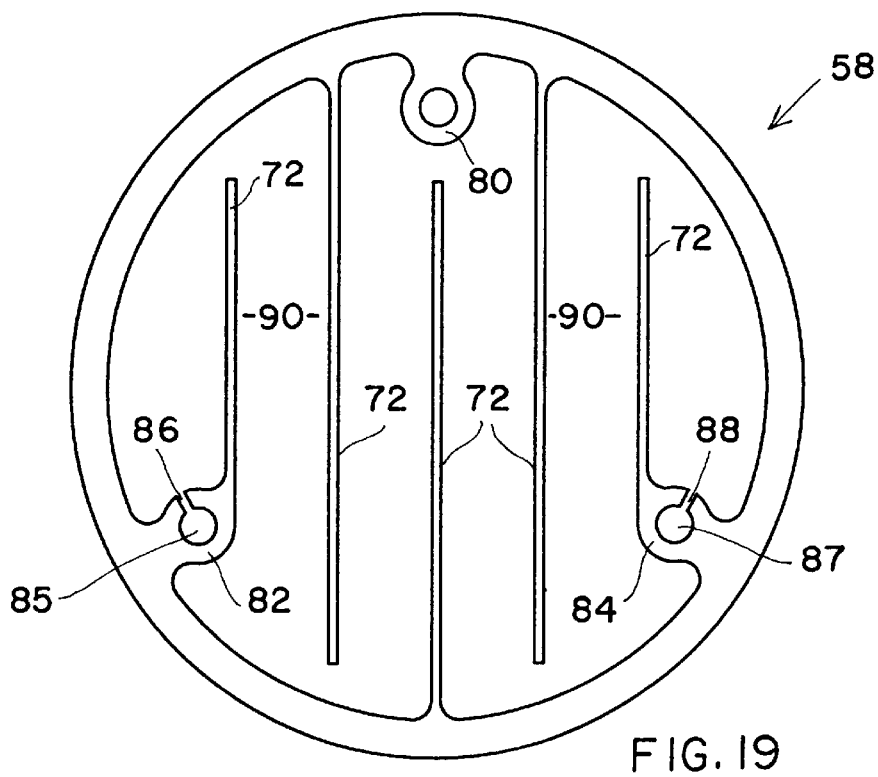
FIG. 19 is a plan view of the CO/$CO_2$ grille in FIG. 15.
Figure 20:
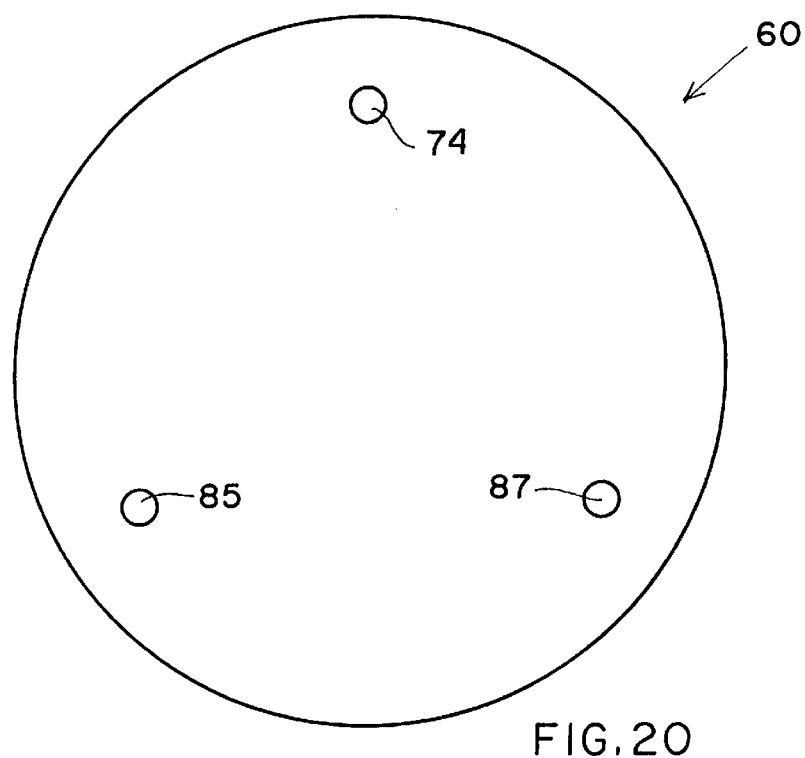
FIG. 20 is a plan view of the diaphragm in FIG. 15.

The grilles are means for distributing both gas and electricity uniformly through the cells. As seen in FIG. 17, for example, the oxygen grille 56 comprises inset channels 70 defined by fingers 72 to confine the product oxygen and convey it to an outlet pipe through a perforation 74 fluidly connected to the outlet pipe 68 by means of a longitudinal manifold running the length of the device, and to distribute voltage uniformly across the adjacent anode. The boundary ring 76 of the grille serves to define a peripheral enclosure to confine the oxygen, while the aperture 78 in the upper outlet ring 80 admits oxygen into the outlet pipe 68. The other two rings 82 and 84 are parts of the $CO_2$ inlet manifold and the $CO/CO_2$ outlet manifold, respectively, and form a seal from the oxygen plenum.

In the preferred embodiment of the invention developed for the described space application, the inside diameters of the small rings 80,82,84 are 0.12 inches, as are the inside diameters of the flow tubes 62,66,68 attached to the bottom plate 56 of the stack. The tubes and rings are sized for a stack of 16 cells, so that the device 50 could be scaled up to 16 cells without changing the design of the cells. The diameters are selected so that all dynamic pressures are less than 1 mbar, thus assuring low pressure differentials throughout the interior of the stack. If the device 50 were constructed with 16 cells, the speed of the oxygen in the outlet tube would be 4.2 m/s, and the dynamic pressure would be 128.6 dynes/$cm^2$, or 28.6 ηbar. Leakage caused by dynamic pressure differentials would be minimal, even with 16 cells in operation.

In addition to flow distribution, the platinum fingers 72 inside the grille 56 distribute electrons across the face of the adjacent electrode. The fingers themselves have constant voltage because they are pressed against or bonded to the top plate. On the other hand, the voltage across the zirconia disk 12 below the grille falls off somewhat between the fingers, according to a theoretical fall-off distance of order $$l = 2[h_{Pt} h_{Zr} \sigma_{Pt}/\sigma_{Zr}]^{1/2}.$$

where $h_{Pt}$ and $h_{Zr}$ are the thicknesses of the platinum electrodes and zirconia electrolyte, respectively, and $\sigma_{Pt}$ and $\sigma_{Zr}$ are their conductivities. Based on electrode and electrolyte thicknesses of about 10 ηm and 0.77 mm, respectively, and conductivities at 1,000° C. of about $2.3 \times 10^6$ mho/m and 10.3 mho/m for platinum and zirconia, respectively, l is calculated to be about 3.3 inches. Since the fingers 72 on the grilles are only about 0.5 inches apart, the voltage distribution is expected to be quite uniform.

It is noted that the oxygen grille 56 of FIG. 17 guides oxygen flow, but to no special purpose because oxygen is the only gas in the plenum. The flow management properties of the $CO/CO_2$ grille 58 of FIG. 19, on the other hand, are much more important. Fresh $CO_2$ enters from the perforation 85 (which is fluidly connected to the inlet pipe 62 by another manifold running the length of the device), through the aperture 86 in the small ring 82 on the lower left, and a mixture of residual $CO_2$ and CO effluent leaves through the aperture 88 in the small ring 84 on the lower right. The perforation 87 in the ring 84 is in turn connected through yet another manifold to the outlet pipe 68, through which the residual gas is exhausted. Thus, the grille 58 guides the gas along a long convoluted channel 90, assuring that no $CO_2$ follows a short circuit from the inlet to the outlet. Turbulent mixing may accomplish the same end, but the well defined flow path formed by the fingers 72 is believed to be preferable.

The grilles 56 and 58 may or may not be diffusion bonded to the adjacent diaphragm or plate. Diffusion bonding would reduce gas leakage, but not bonding the grilles makes it possible to modify and test new grille geometries without altering other parts of the stack.

Figure 22:
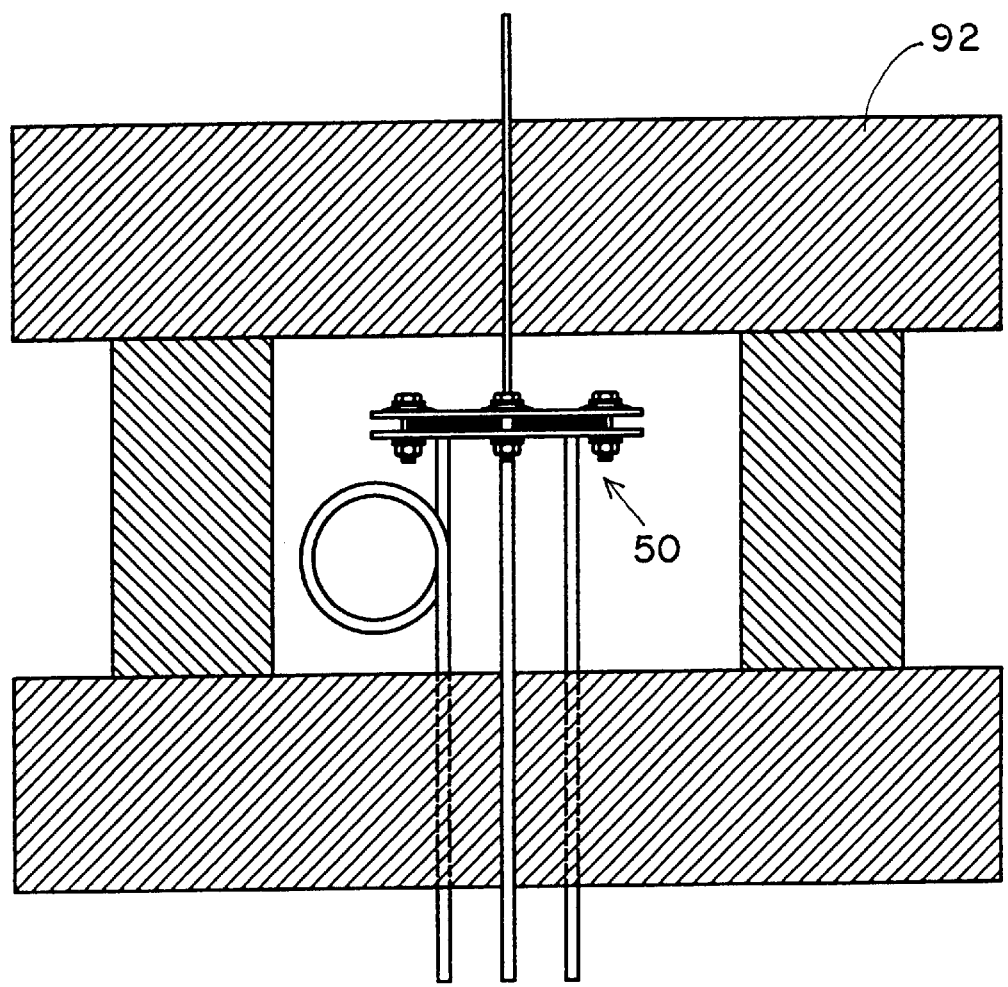
FIG. 22 is a schematic elevational view of the device of the invention contained in an insulated heater element.

In use, the device 50 of the invention is enclosed in a thermally insulated heater 92 required to reach and maintain, if necessary, the desired operating temperature. Such an arrangement is illustrated schematically in FIG. 22.

On the basis of the foregoing, a novel means for accomplishing solid-oxide electrolysis has been established, one that is particularly well suited to the rigors of space flight and autonomous operation on Mars. Instead of the polycrystalline ceramics used in the past, which are brittle and liable to break under thermal and mechanical shocks, the new approach utilizes single crystals of zirconia combined with electrical and structural components made with metals carefully selected to optimize electrical and thermal efficiencies. The result is a compact and robust electrolysis cell, more nearly resembling a solid state device than a chemical plant.

The concepts of the invention are equivalently applicable to fuel-cell and oxygen-sensor applications, with necessary adaptations that would be obvious to one skilled in the art. Similarly, the invention has been described in terms of stabilized zirconia, but other solid oxides that are known to perform equivalently in ceramic form would be expected to also be suitable to practice the invention. Such materials include, without limitation, $Al_2O_3$, $Y_2O_3$, $CeO_3$, and various formulations of oxygen-ion-conducting Perowskites, all stabilized with dopants such as $Y_2O_3$, $Nd_2O3$, $Sm_2O_3$, $Yb_2O_2$ and $Sc_2O_3$, as is well understood in the art.

Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

I claim:

1. A device for solid-oxide electrolytic-cell and fuel-cell applications comprising the following components:

a single-crystal solid-oxide component having a first surface facing a first enclosure and a second surface facing a second enclosure;

electrode material applied to each of said first and second surfaces;

electrical connections to each of said surfaces to establish an electrical potential across the surfaces when the device is used as an electrolytic cell or produce an electrical potential across the surfaces when the device is used as a fuel cell; and inlet and outlet ports connected to said first and second enclosures to provide feed gas and exhaust product gas from the device.

2. The device of claim 1, wherein said solid-oxide component consists of stabilized zirconia.

3. The device of claim 1, wherein said electrode material consists of platinum.

4. The device of claim 1, wherein said solid-oxide component consists of stabilized zirconia and said electrode material consists of platinum.

5. The device of claim 1, further comprising a heater adapted to maintain said single-crystal solid-oxide component and said first and second enclosures substantially at a predetermined temperature.

6. A multilayered device for solid-oxide electrolytic-cell and fuel-cell applications comprising:

(a) a plurality of axially stacked cells, each cell comprising
      a first grille defining a first peripheral enclosure; a second grille defining a second peripheral enclosure;
      a single-crystal solid-oxide component having a first surface facing said first grille and a second surface facing said second grille, said solid-oxide component being adapted to mate the first surface with said first grille and the second surface with said second grille to form sealed connections;
      electrode material applied to each of said first and second surfaces of the solid-oxide component; and
      electrical connections to said first and second surfaces of the solid-oxide component to establish an electrical potential across the surfaces when the device is used as an electrolytic cell or produce an electrical potential across the surfaces when the device is used as a fuel cell;

(b) diaphragm means for connecting pairs of said cells in sealed pile arrangement to form a stack of cells;

(c) a first end plate adapted to mate with said first grille, such as to seal a first end of said stack of cells;

(d) a second end plate adapted to mate with said second grille, such as to seal a second end of said stack of cells; and (e) inlet and outlet ports connected to said first and second grilles to provide feed gas to the device and exhaust product gas from the device.

7. The device of claim 6, wherein said single-crystal solid-oxide component consists of stabilized zirconia.

8. The device of claim 6, wherein said electrode material consists of platinum.

9. The device of claim 6, wherein said first and second grilles, said diaphragm means, and said first and second end plates are made of platinum.

10. The device of claim 6, wherein said solid-oxide component consists of stabilized zirconia, said electrode material consists of platinum, and said first and second grilles, said diaphragm means, and said first and second end plates are made of platinum.

11. The device of claim 6, wherein said inlet and outlet ports include manifolds connecting all cells through perforations in said first and second grilles, said single-crystal solid-oxide components, and said diaphragm means.

12. The device of claim 6, wherein said first and second grilles comprise flow channels to control fluid flow within the grilles.

13. The device of claim 10, wherein said inlet and outlet ports include manifolds connecting all cells through perforations in said first and second grilles, said single-crystal solid-oxide components, and said diaphragm means.

14. The device of claim 13, wherein said first and second grilles comprise flow channels to control fluid flow within the grilles.

* * * * *